United States Patent [19]
Causton

[11] Patent Number: 5,885,552
[45] Date of Patent: Mar. 23, 1999

[54] MOUTHRINSE

[75] Inventor: Brian Edward Causton, Aldermaston, United Kingdom

[73] Assignee: Gillette Canada Inc., Kirkland, Canada

[21] Appl. No.: 492,069

[22] PCT Filed: Jan. 19, 1993

[86] PCT No.: PCT/US92/11083

§ 371 Date: Jul. 19, 1995

§ 102(e) Date: Jul. 19, 1995

[87] PCT Pub. No.: WO94/16673

PCT Pub. Date: Aug. 4, 1994

[51] Int. Cl.⁶ ............................................. A61K 7/16
[52] U.S. Cl. ................. 424/49; 424/48; 424/435
[58] Field of Search .......................... 424/49, 48

[56] References Cited

U.S. PATENT DOCUMENTS

| | | | |
|---|---|---|---|
| 4,260,597 | 4/1981 | Porteous | 424/49 |
| 4,473,373 | 9/1984 | Ryan | 424/54 |
| 4,816,245 | 3/1989 | Gaffar | 424/57 |
| 4,857,303 | 8/1989 | Grollier | 424/52 |
| 4,913,894 | 4/1990 | Curtis et al. | 424/49 |
| 4,915,936 | 4/1990 | Patterson et al. | 424/49 |
| 4,980,150 | 12/1990 | Keith | 424/49 |
| 5,011,830 | 4/1991 | Leonard et al. | 424/57 |
| 5,230,895 | 7/1993 | Czarnecki et al. | 424/422 |
| 5,310,647 | 5/1994 | Kerchensteiner | 435/4 |
| 5,401,723 | 3/1995 | Gaffar et al. | 514/21 |

FOREIGN PATENT DOCUMENTS

| | | |
|---|---|---|
| 0 346 097 A3 | 12/1989 | European Pat. Off. . |
| 2 603 801 | 3/1988 | France . |
| WO 86/02831 | 5/1986 | WIPO . |
| WO 90/00387 | 1/1990 | WIPO . |
| WO 92/03124 | 3/1992 | WIPO . |

*Primary Examiner*—Thurman K. Page
*Assistant Examiner*—William E. Benston, Jr.
*Attorney, Agent, or Firm*—Chester Cekala

[57] ABSTRACT

A three-component mouthrinse comprises a mouthrinse active material e.g. bactericide, a polymeric material e.g. polysaccharide which can be gelled in the mouth, and means (e.g. a polyacid) for gelling the polymeric material to form a water-insoluble gel in the mouth, from which gel the active material is slowly released.

14 Claims, No Drawings

MOUTHRINSE

This application is a 371 of PCT/US92/11083 filed Jan. 19, 1993.

This invention relates to a mouthrinse and to its use.

It is well known to use a mouthrinse composition to provide various orally active materials in the mouth cavity. There is a problem, however, in maintaining an effective concentration of these materials in the mouth over a period of time because, after use of the mouthrinse, the normal flushing of gums and teeth by saliva tends to wash away the deposited mouthrinse materials. Although some highly charged cation materials do adsorb preferentially on to the buccal mucosa and are slowly released therefrom, many other mouthrinse materials become diluted and are removed from the mouth much more quickly than is desirable.

We have now found a way in which this problem can be reduced or eliminated. According to the present invention, we provide in the mouthrinse a material which, when in the mouth, can be gelled to form a water-insoluble thin coating from which the active material is slowly released over a period of time. In this way, effective concentrations of active material can be maintained in the mouth for extended periods after use of the mouthrinse.

According to the present invention, there is provided a three component mouthrinse which comprises (a) a mouthrinse active material, (b) a polymeric material which can be gelled when in the mouth, and (c) means for gelling the polymeric material in the mouth, to form a water-insoluble gel in the mouth from which gel the active material is slowly released over a period of time, wherein each of components (a), (b) and (c) is in aqueous solution for rinsing the mouth.

The invention also includes a method of depositing an active material for slow release in the mouth, which comprises rinsing the mouth with a mouthrinse according to the invention, to form in the mouth a water-insoluble gel containing the active material.

The mouthrinses of the invention have three essential components (a), (b) and (c) as defined above, and these components are each in either aqueous solution or aqueous mixtures with other safe solvents such as ethanol, so that they are suitable for rinsing the mouth. In one embodiment of the invention, all three components can be in admixture in a single solution, whereas in other embodiments the components may be used separately or in sub-mixtures in which case the mouthrinse will comprise two, or three individual solutions to be used to rinse the mouth sequentially. The preferred mouthrinses of the invention consist of a single aqueous solution containing all three components.

Component (a) is an active material for slow release into the oral cavity. There are many such active materials which are conventionally administered by mouthrinses, among which materials are, for example, bactericides, anti-inflammatories, remineralising solutions, fluorides, desensitisers, antifungal agents, salivary gland stimulators, deodorants and antibiotics. In accordance with the invention, this mouthrinse active material (component (a)) becomes encapsulated or trapped within the gel which forms in the mouth, and is released only slowly therefrom to maintain an effective concentration of the material in the mouth over a considerable period of time following use of the mouthrinse.

The precise nature of components (b) and (c) will depend on whether the mouthrinse is to be in the form of a single solution (containing all three components) or whether it is to consist of two (or three) separate solutions. The preferred arrangement is the single solution and this will now be described. In a most preferred embodiment of the single solution mouthrinse of the invention, component (b) is a polymer which gels in the presence of dissolved calcium ions, and component (c) is an etchant polyacid capable of releasing calcium ions into solution when in contact with teeth. In use of this embodiment of mouthrinse of the invention, the aqueous solution first wets a tooth surface, and the acid dissolves any pellicle present and then releases calcium ions from the enamel cuticle beneath. The calcium ions are released into solution as the soluble calcium salt of the acid. The calcium ions diffuse into the mouthrinse solution on the tooth and precipitate the calcium-sensitive polymer. Thus, a hydrophilic film of gelatinous polymer is formed on the tooth, from which film the active material in the mouthrinse can diffuse into the mouth over a period of time. The nature of the gelation process is such that the gel only forms on the tooth surface where calcium ions are available.

If the polymer solution is coated on teeth in the absence of any etchant acid, no gelling occurs. This is in contrast to certain prior art mouthrinse compositions in which polymeric coatings on teeth are formed by contacting the teeth with a solution of a copolymer which, when in contact with the calcium containing teeth surface, is gelled to form an adherent coating on the teeth. No etchant acid is used or needed. Examples of such mouthrinses are given in, for example, U.S. Pat. No. 5,015,467 which describes oral care compositions for preventing the accumulation of calcium and plaque on teeth. In these compositions, gelling occurs as a result of contact between the polymer and the teeth, whereas in the present invention no such gelling will occur unless an acid etchant is present to provide dissolved calcium ions.

In accordance with the invention, the gel layer can be removed periodically by tooth brushing to avoid any unsightly build-up of gel. The mechanical strength of the gel ensures its retention only in areas of stagnation, e.g. interproximal areas, occlusal pits and fissures. As the polyacid continues to etch the enamel surface, the increased ionic strength of the interstitial solution causes the gel to contract. Gels formed in this way are not dissolved by saliva, but are merely swollen by is as the natural buffering effect of the saliva first adjusts the final pH of the gel to about 7.4 and infiltrates the gel with phosphate, sodium and chloride ions in isotonic balance with the rest of the oral environment. The thickness of the layer can be further controlled by varying the molecular weight and functionality of the polyacid and the gelling polymer, higher molecular weights producing thicker layers. The more polyacid groups there are present, the more efficient the surface cleansing action.

The gel so formed on teeth in the mouth carries the active material(s) of the mouthrinse for slow release over a period of time. In this way, an effective concentration of the active material(s) can be maintained in the mouth for considerable periods after use of the mouthrinse.

Any orally non-toxic acid capable of releasing calcium ions from teeth enamel into solution may be used, monomeric or polymeric, in these preferred mouthrinses of the invention, but we much prefer to use polyacids because of the mild nature of their attack on the tooth surface. We prefer to use poly(acrylic acid) or its copolymers but other etchant polyacids and their copolymers can be used. These include other carboxylic acids, e.g. methacrylic, and other polyacids such as phosphate, phosphonic, phosphinic, sulphonic, sulphinic, sulphamic etc. Copolymers of polyacids, whether block, random or graft, can be used to improve hydrophilicity by including vinyl pyrrolidone, polyethylene oxide, hydroxyalkyl(meth)acrylate, acrylamides, methacrylamides, aminoalkyl(meth)acrylates etc. In general, polycarboxylic acids and copolymers thereof, both saturated and unsaturated, are useful (e.g. copolymers of poly(acrylic acid) with itaconic or maleic acid). In all cases, the etchant acids must form soluble calcium salts. The invention does not encompass the use of etchant acids which themselves form insoluble calcium salts on the teeth.

The preferred polymers for use in this embodiment of the invention are alginates since these are readily precipitated from aqueous solution by dissolved calcium ions, e.g. carboxymethylcellulose (sodium salt) carrogeenans, agar, guar gums etc. However, other polysaccharides and derivatives thereof can be used, as can protein-based salts and the salts of synthetic polymers such as polystyrene sulphonate. Also polyvinyl alcohol and its derivatives can be used, as can polyethylene vinylacetate derivatives although there can be taste problems here. Acidic polymers which gel directly on contact with teeth are not used as such in the present invention. They may instead be converted to a neutral non-etching form, e.g. a sodium salt, and then used if appropriate.

The properties of the gel formed when the single solution mouthrinse is in contact with a tooth, can be enhanced by using a polymer and an acid which can coacervate. In such cases, however, solvation of the polyacid must be suppressed to prevent premature coacervation in the bottle before use of the mouthrinse. Coacervation in the bottle (or other container) can be prevented by adding an alcohol or similar solvent, e.g. propylene glycol, to the solution. In many formulations, alcohol is in any case needed as a necessary solvent for the active material; the tolerance of the system to alcohol is hence a virtue under such circumstances. In use of the single solution mouthrinse, as the alcohol is lost from the gelling coating on a tooth, coacervation occurs so consolidating the gel.

Good results in terms of gel formation are obtained by using poly(acrylic acid) as the acid and sodium alginate as the gellable polymer. Both are inexpensive and not orally toxic. Sodium alginate is used in soups, and poly(acrylic acid) has been used in dental cements for more than twenty years. The attack of poly(acrylic acid) on the enamel of teeth is mild, being no worse than that of some soft drinks. Sodium alginate precipitates irreversibly in the presence of dissolved calcium ions. If poly(acrylic acid) is to be used with polyether-containing non-ionics, alcohol must be included in the mouthrinse to prevent premature coacervation. Whilst the molecular weight of the sodium alginate used does not appear to be critical, it is advisable to use a poly(acrylic acid) of molecular weight above about 5000.

The components of the single solution mouthrinses of the invention can, of course, be formulated as two, or three, separate solutions for appropriate sequential rinsing of the mouth but there is no advantage in this and, indeed, it is generally disadvantageous. There are, however, other components (b) and (c) which necessarily, or advantageously, are kept as separate solutions and are not mixed but are used for sequential rinsing, so that mixing only occurs in the mouth. Examples of these components are, for component (b), cationic polymers which preferentially adsorb on the mucosa. One example is quaternised poly(chloroacetate) sodium salt. Subsequent rinsing with (as component (c)) an anionic polymer which coacervates with the cationic polymer, for example poly(acrylic acid), causes a thin layer of gel to form on the mucosa. The mouthrinse active material (component) (a)) can be mixed with either component (b) or more preferably component (c), or it can be applied separately.

Another example of a mouthrinse system of the invention which is in the form of two (or three) separate solutions, is that in which component (b) is a polymer which preferentially binds to the collagen in the dentine on teeth, for example dextran sulphate, and component (c) is cationic polymer which coacervates with component (b), for example polybisguanide. Again, component (a) can be mixed in with component (b) or, more preferably, with component (c), or it can be kept separate.

As will be appreciated by those skilled in the art, the two- or three-solution mouthrinses are useful where it is difficult or impractical to combine all the components prior to use. Such formulations do, however, enable different types of gels to be used which can be selectively deposited in different regions of the oral cavity. This can have advantages in connection with the effectiveness of the mouthrinse in providing any particular active material in the mouth.

In all cases, the mouthrinses of the invention whether they consist of single solutions, or of two or more separate solutions, of the components, are in liquid form for use in rinsing the mouth. The viscosity of any solution must not be such that ordinary mouth rinsing is made difficult or impossible.

The mouthrinses of the invention have been described in terms of three essential components (a), (b) and (c). They can, of course, include other substances as necessary or desirable, provided that these other substances do not deleteriously affect the mouthrinse.

In order that the invention may be more fully understood, the following Examples are given way way of illustration only.

EXAMPLE 1

To 0.25 g of poly(acrylic acid), of molecular weight 30,000, in 20 ml of distilled water, a 100 ml aliquot of 1% sodium alginate in water is added with stirring. The solution, when placed in contact with a visking tube containing a 10% calcium acetate solution, quickly forms a gel layer on the outer surface of the tube. The same solution, when placed on a clean human tooth, similarly forms a gel layer. A thirty second exposure of tooth to the solution results in the formation of a gel layer about 200 $\mu$m thick.

EXAMPLES 2–6

The following stock solution was made up:

| | |
|---|---|
| Sodium alkinate (food grade) | 1 g |
| Poly acrylic acid (Versicol E7 (25%, MW 30M) | 1 g |
| Water | 120 g |

Various compositions of the invention were made by adding mouthrinse active materials to this stock solution during high speed stirring. In those cases where the active caused the stock solution to either gel or precipitate, ethanol was added to suppress ionic interaction.

2. Chlorhexidine Gluconate

Using 15% alcohol, a cloudy stable solution of 0.5% chlorhexidine di gluconate in the stock solution was made. A preferred composition contains 15% ethanol and 0.15% chlorhexidine digluconate.

3. Cetyl Pyridinium Chloride (CPC)

The addition of 10% ethanol was necessary to produce a stable cloudy solution of 0.1% CPC. Higher concentrations of ethanol (15%) could be used but there is little advantage to be gained by increasing the alcohol content from 10 to 15% when incorporating CPC into the stock solution.

4. Sodium Fluoride

The addition of 1% sodium fluoride to the stock solution had no noticeable effect. Adding 5% sodium fluoride turns the stock solution cloudy, and precipitation occurs at levels of sodium fluoride above 10%.

5. Strontium Fluoride

If strontium fluoride (0.15%) and ethanol (15%) are added with vigorous stirring to the stock solution, the resultant mixture is slightly turbid but the strontium does not cause the solution to gel excessively. The rheology of the formulated solution is highly pseudoplastic. This pseudoplasticity has advantages when rinsing since the gel resides most in the low shear, stagnant parts of the mouth.

6. Nystatin

Nystatin dissolves easily in the stock solution without precipitation.

EXAMPLE 7

Flavouring trials on all the above mentioned solutions in their 15% ethanolic form were carried out on a panel of twelve volunteers, six men and six women, by including various flavours in the compositions.

A typical gel used in the trial is:

| | |
|---|---|
| Stock solution | 84.775 g |
| EtOH | 15.000 g |
| Chlorhexidine | 0.150 g |
| Saccharine | 0.015 g |
| Flavour | 0.60 g |

This trial showed that the tests of the polymers and actives could be masked by flavouring with no loss of activity as shown in Example 9.

EXAMPLE 8

Surgically removed human second molars were stored in eetrimide solution. The surface of each tooth was coated with nail varnish, with the exceptions of four 2 mm square windows on the buccal surface and four similar windows on the lingual surface. Compositions of the invention described above were applied to each window and removed after either ½ minute, 1, 1.5 or 2 minutes. The after treatment surfaces were washed with distilled water, then allowed to dry prior to gold coating and viewing in the scanning electron microscope. All gel solutions covered the enamel surface, with increased coverage with time. The presence of active layed down on the tooth was demonstrated by fluorescence microscopy.

EXAMPLE 9

A strain of streptacoccus mutans was purchased and grown into a culture on blood agar plates. The test consisted of inoculating, with the culture agar plates that contained wells filled with mouthrinse. The plates were examined at 16 and 21 hours.

The gels containing chlorhexidine and CPC showed bacteriocidal activity. At 21 hours, the inhibition of these two gels is total.

The large areas of inhibition around the two gels show that the active bacterocides migrated from the gels, i.e. were released thereby.

EXAMPLE 10

Example 1 was repeated using, in place of the poly(acrylic acid) (a) a copolymer of acrylic acid and maleic acid (50/50), and (b) a copolymer of acrylic acid and maleic acid (75/25). Both copolymers were prepared by the method described by A. A. El'Said et al., Polym. Sci. USSR, 11, 314 (1969), and were used as 43 w/w % solutions of viscosity 12 Poise (1.2 Pa s). The results were similar to those in Example 1. Both the copolymers formed gel layers. The 50/50 copolymer gel was the stronger.

EXAMPLE 11

Copolymers of acrylic and itaconic acids were made as described in Example 10 and used in place of poly(acrylic acid) in a repeat of Example 1. The results were similar to those in Example 1. The acrylic/itaconic acid gels were not as strong as the acrylic/maleic gels of Example 10.

EXAMPLE 12

Example 1 was repeated using, in place of the poly(acrylic acid), a poly(vinyl phosphonate) made in the manner described by Anbar et al., J. Dent. Res., 53, 867 (1974). Gel formation was slower than in Example 1 and the gel formed was weaker. However, when 1% sodium fluoride was incorporated into the ungelled mixture, gel formation was much more rapid and there was an improvement in gel strength.

EXAMPLE 13

When Example 1 is repeated using methacrylic acid (molecular weight 40,000) instead of the poly(acrylic acid), the gel formation is slower than in Example 1 and the gel formed is softer.

EXAMPLE 14

Example 1 was repeated using, instead of the sodium alginate solution, a 5% aqueous solution of dextran sulphate (molecular weight 50,000). The mixture (with the poly (acrylic acid)) is stable and, upon contact with the visking tube, gelling occurred as in Example 1.

EXAMPLE 15

Example 1 was repeated using, in place of the sodium alginate solution, a 2% solution of carboxymethyl cellulose sodium salt (molecular weight 3000–6000). The gel formed more slowly than in Example 1 and was softer and more easily broken.

EXAMPLE 16

Example 2 was repeated using, in place of the 15% ethanol, urea to a concentration of 10%. A stable solution resulted. Acetone and methanol can also be used in place of the ethanol of Example 2, but the mouthwash would then need to be painted on to the teeth by a clinician. Glycols (e.g. propylene glycol) and propylene carbonate can also be used as substitutes for the ethanol in Example 2.

EXAMPLE 17

By way of illustration of a coacervating system, to a quaternised poly(vinyl chloracetate) (molecular weight 14,000) 4% in ethanol, was added an aqueous 25% solution of poly(acrylic acid) (of molecular weight 30,000). The two solutions can be mixed in equal proportions to form a stable emulsion. Upon the introduction of calcium ions (e.g. as calcium acetate or via a dialysis bag as in Example 1), the emulsion flocculates. If this is accompanied by loss of alcohol (as in use of the mouthrinse), a stable dense gel forms that is insoluble in water. The polymer used in this Example, via. Quaternised poly(vinyl chloracetate) is substantive to both tooth and mucosa.

EXAMPLE 18

To the stock solution used in Examples 2 to 6 was added 0.15% chlorohexidine gluconate, 0.015% strontium fluoride and 0.10% sodium fluoride. When this mixture was tested as in Example 9, an area of inhibition 8 times that obtained from the chlorohexidine gel (of Example 2) was obtained. Neither the strontium fluoride nor the sodium fluoride when used separately showed any bacteriocidal effect.

EXAMPLE 19

Examples 2 to 6 show the use of various active materials in the mouthrinses of the invention. Other active materials which can similarly be included in the mouthrinses are: hydrocortisone (anti-inflammatory), sodium citrate (salivary gland stimulator), penicillin (antibiotic). Sodium fluoride can be used as a remineralising solution or as a source of fluoride; strontium fluoride can be used as a desensitiser, or as a source of fluoride; nystatin can be used as an antifungal agent; and cetyl pyridinium chloride can be used as a bactericide or as a deodorant.

I claim:

1. A method of dispensing an active material for slow release in the mouth, which comprises rinsing the mouth with a mouthrinse to form in the mouth a water-insoluble gel containing the active material, said mouthrinse comprises (a) a mouthrinse active material, (b) an orally non-toxic polymeric material which can be gelled when in the mouth in the presence of dissolved calcium ions and (c) an orally non-toxic etchant acid capable of releasing calcium ions into solution when in contact with teeth to form a water-insoluble gel in the mouth from which gel the active material is slowly released over a period of time, wherein each of components (a), (b) and (c) is in aqueous solution.

2. A method according to claim 1, wherein the acid is a water-soluble polyacid.

3. A method according to claim 2, wherein the polyacid is poly(acrylic acid) or an acidic acrylate, methacrylate, phosphate, phosphonate, phosphinate, sulphate, sulphonate or sulphinate polymer, the polyacid having a water-soluble calcium salt.

4. A method according to claim 2, wherein the polyacid is a copolymer of an acidic monomer and one or more of vinyl pyrrolidone, ethylene oxide, hydroxyethylmethacrylate, an acrylamide or methacrylamide, the polyacid having a water-soluble calcium salt.

5. A method according to any of claims 1, wherein the polymer is a polysaccharide, a protein based salt, or a salt of a synthetic polymer.

6. A method according to claim 5, wherein the polymer is an alginate.

7. A method according to any of claims 6, wherein the polymer and the acid will coacervate, and an organic solvent is included in the composition to prevent organic solvent is included in the composition to prevent coacervation before use of the mouthrinse.

8. A method according to claim 7, wherein the solvent is an aliphatic alcohol.

9. A mouthrinse according to claim 1, which comprises an aqueous solution of component (b) and a separate aqueous solution of component (c).

10. A mouthrinse according to claim 9, wherein component (b) is a cationic polymer, and component (c) is an anionic polymer, the anionic and cationic polymers being such as will coacervate of mixing.

11. A mouthrinse according to claim 10, wherein component (b) or component (c) is a polymer which will preferentially bind to a particular region of the mouth.

12. A mouthrinse according to claim 11, wherein component (b) is a polymer which will preferentially bind to the mucosa, or to the collagen in the dentine of teeth.

13. A mouthrinse according to claim 12, wherein component (a) is in the aqueous solution of component (c).

14. A mouthrinse according to any of claims 13, wherein component (a) is a bactericide, an anti-inflammatory material, a remineralising solution, a fluoride, a desensitiser, an antifungal agent, a salivary gland stimulator, a deodorant or an antibiotic active drug, or any mixture of two or more thereof.

* * * * *